United States Patent
Kakavand et al.

(10) Patent No.: US 8,517,726 B2
(45) Date of Patent: Aug. 27, 2013

(54) DENTAL APPLIANCE WITH RESILIENT PORTION

(75) Inventors: Ali Kakavand, San Carlos, CA (US); Vadim Matov, San Jose, CA (US); Jennifer C. Chen, San Francisco, CA (US); Jon F. Moss, Antioch, CA (US); Jihua Cheng, Cupertino, CA (US)

(73) Assignee: Align Technology, Inc., San Jose, CA (US)

( * ) Notice: Subject to any disclaimer, the term of this patent is extended or adjusted under 35 U.S.C. 154(b) by 359 days.

(21) Appl. No.: 12/283,567

(22) Filed: Sep. 12, 2008

(65) Prior Publication Data

US 2010/0068671 A1 Mar. 18, 2010

(51) Int. Cl.
*A61C 7/08* (2006.01)

(52) U.S. Cl.
USPC .................................. 433/6; 433/8; 433/18

(58) Field of Classification Search
USPC .................. 433/6, 18, 2, 5, 7, 19, 20–22, 24, 433/8–17, 23
See application file for complete search history.

(56) References Cited

U.S. PATENT DOCUMENTS

| | | | |
|---|---|---|---|
| 3,464,114 A * | 9/1969 | Brader | 433/10 |
| 3,803,715 A | 4/1974 | Wallshein | |
| 4,880,380 A * | 11/1989 | Martz | 433/11 |
| 5,013,239 A * | 5/1991 | Kesling | 433/6 |
| 6,183,248 B1 | 2/2001 | Chishti et al. | |
| 6,702,575 B2 | 3/2004 | Hilliard | |
| 7,104,790 B2 * | 9/2006 | Cronauer | 433/6 |
| 7,121,825 B2 | 10/2006 | Chishti et al. | |
| 2002/0106604 A1 | 8/2002 | Phan et al. | |
| 2004/0009449 A1* | 1/2004 | Mah et al. | 433/7 |
| 2004/0048223 A1 | 3/2004 | Phan et al. | |
| 2004/0170941 A1* | 9/2004 | Phan et al. | 433/6 |
| 2006/0008760 A1* | 1/2006 | Phan et al. | 433/6 |
| 2006/0188834 A1 | 8/2006 | Hilliard | |
| 2006/0234179 A1 | 10/2006 | Wen et al. | |
| 2006/0269891 A1* | 11/2006 | Miqui | 433/16 |
| 2010/0075268 A1* | 3/2010 | Duran Von Arx | 433/6 |
| 2010/0239992 A1 | 9/2010 | Brandt et al. | |

* cited by examiner

*Primary Examiner* — Cris L Rodriguez
*Assistant Examiner* — Edward Moran
(74) *Attorney, Agent, or Firm* — Brooks, Cameron & Huebsch, PLLC

(57) ABSTRACT

Methods and devices utilizing a dental appliance having a resilient portion are disclosed. One such appliance is a removable dental positioning appliance that includes, a plurality of shell portions each having one or more cavities shaped therein to receive one or more teeth and wherein each of the plurality of shell portions is formed to be separate from each of the other plurality of shell portions; a resilient component attached to a side of at least two shell portions; and wherein at least one of, the resilient component and one or more of the shell portions, provides one or more forces to reposition one or more teeth from a first orientation to a successive orientation.

24 Claims, 5 Drawing Sheets

DENTAL APPLIANCE WITH RESILIENT PORTION

BACKGROUND

The present disclosure is related generally to the field of dental treatment. More particularly, the present disclosure is related to using a dental positioning appliance to facilitate the movement of one or more teeth.

Some dental processes use positioning appliances for realigning teeth (e.g., some orthodontic processes). Such appliances may utilize a thin shell of material having resilient properties, referred to as an "aligner", which generally conforms to a patient's teeth but is slightly out of alignment with the initial tooth configuration.

Placement of such an appliance over the teeth provides controlled forces in specific locations to gradually move the teeth into a new configuration. Repetition of this process with successive appliances that provide progressive repositioning may eventually move the teeth through a series of intermediate arrangements to a final desired arrangement, which then may allow positioning of the dental implant to occur at that time.

Another alignment technique is the use of metallic bands that are attached to teeth by a treatment professional. These bands cannot be easily removed by the patient and typically include a metallic bracket on the side of the band that is to be positioned on the buccal side of a tooth. Brackets may also be bonded directly to the tooth surface. Then, a rubber band or other suitable ligature is used to retain a pre-bent wire to each bracket. Some brackets are designed to incorporate a self-ligating feature that is integral to the bracket.

The pre-bent wire is pre-bent by the treatment professional. The accuracy of such bending is dependent upon a number of factors including the expertise of the treatment professional, the tools used, and the information used to determine the shape of the wire.

Since the bands and/or brackets generally cannot be removed without the assistance of a treatment professional, they can be uncomfortable and/or difficult to keep clean thus leading to the potential increase of dental caries. Further, since the bands around the teeth, wire, and rubber bands are generally opaque, the patient may feel awkward wearing the apparatus in some situations. Such an apparatus may be particularly identifiable based upon the presence of the wire and/or brackets on the buccal side of the teeth.

DETAILED DESCRIPTION

Methods and devices utilizing a dental appliance having a wire portion are disclosed. For example, one such removable dental positioning appliance includes, a polymeric shell having a plurality of cavities shaped to receive and reposition one or more teeth from a first orientation to a successive orientation, and wherein each of the plurality of cavities is formed to be separate from each of the other plurality of cavities, and a resilient component attached to a side (i.e., an outer lingual or buccal side of the shell portion forming a cavity) of at least two cavities of the shell.

Figure 1:
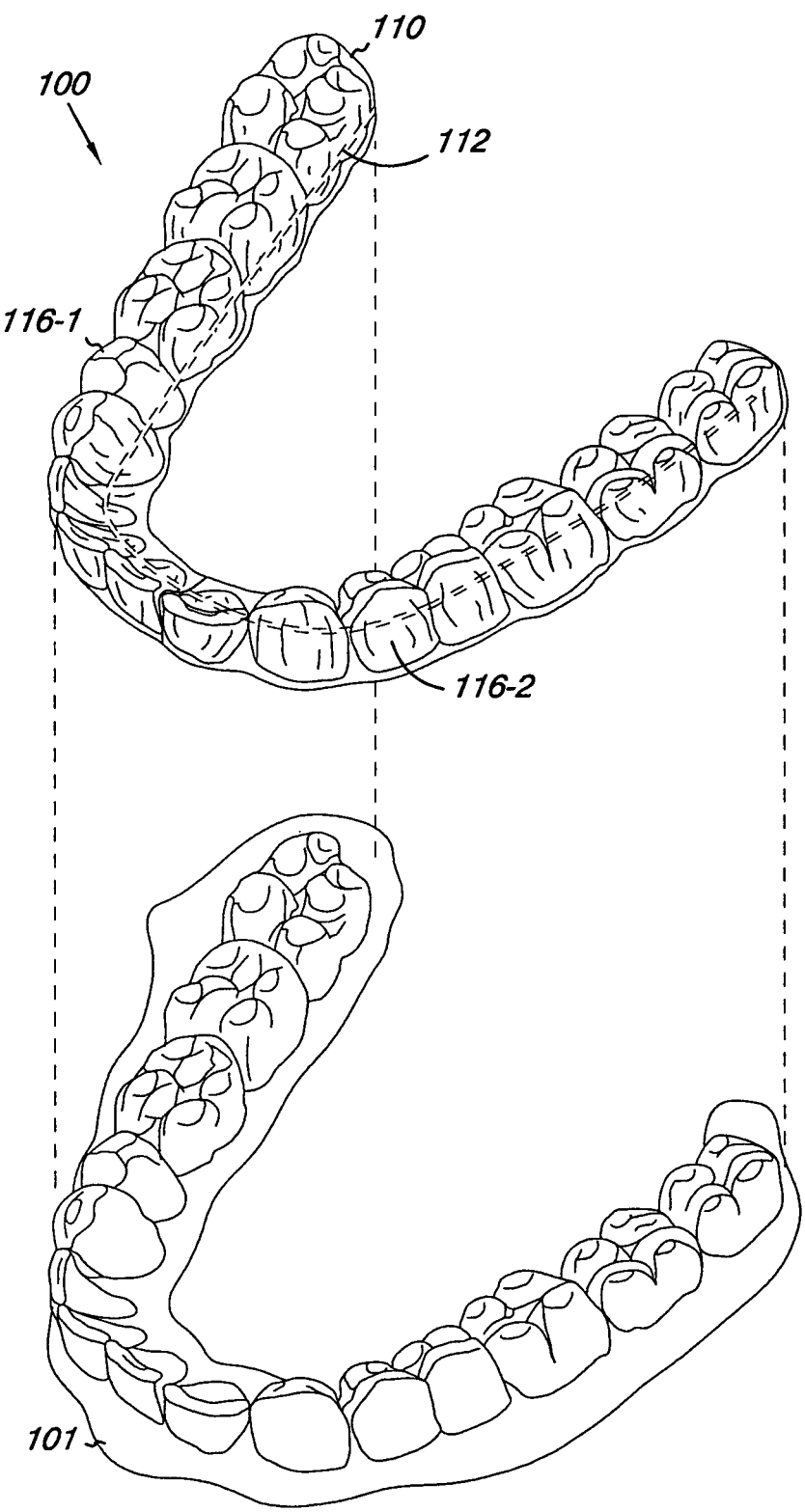
FIG. 1 illustrates a lower jaw of a patient together with an example of a dental positioning adjustment appliance embodiment of the present disclosure.

FIG. 1 illustrates a lower jaw of a patient together with an example of a dental positioning adjustment appliance embodiment of the present disclosure. As described in the present disclosure, embodiments of dental positioning adjustment appliances, as illustrated in FIG. 1, can include an appliance 100 (which, as described in the present disclosure, can be termed "aligners") formed from a shell 110 and a resilient component 112 (e.g., a wire portion).

The shell can have portions, or the entire shell, made from a polymeric material. For example, the buccal side (i.e., side of the shell to be positioned on the side of the tooth near the cheek or lips) of the shell, or portions thereof, can be formed from a polymeric material and the lingual side (i.e., side of the shell to be positioned on the side of the tooth near the tongue) of the shell or portions thereof can be made from another material (e.g., metallic). In some embodiments, the portions made from first material (e.g., metallic) can be coated with, provided over, or encapsulated within a second material (e.g., polymeric).

In some embodiments, the shell includes a plurality of cavities (e.g., 116-1, 116-2) used to receive one or more teeth (e.g., eight teeth in cavity 116-1, seven teeth in cavity 116-2) in each such cavity. The shell portions that are to be positioned on the buccal side of the teeth can be formed from a transparent material (e.g., a transparent polymeric material). This may allow the appliance to substantially not be visible to people looking at the patient's mouth, among other benefits.

In some embodiments, the entire appliance may be made from such a transparent material and/or, in some embodiments, the resilient component can be made from such a material. A resilient component material and/or attachment members used to attach the resilient component to the one or more shell portions may be the same material used to make other portions of the shell, or the entire shell, and the resilient component material and the one or more shell materials may or may not have the same resiliency. It is to be understood that the shape, size, and/or coverage of the appliance 100 is presented by way of example in the figures of the present disclosure and not by way of limitation.

The resilient component 112 can be attached to the plurality of cavities that are used to receive one or more teeth in various manners. Various examples of suitable attachment types are discussed in more detail below.

In the embodiment of FIG. 1, the resilient component is embedded in the surface of the shell 110. This can be accomplished during fabrication of the shell 110 or an aperture can be provided in the one or more shell portions and the resilient component can be positioned in the aperture, among other methods of embedding such a component therein.

In some embodiments, the assembly of the one or more shell portions and the resilient component can be accomplished by a treatment professional. In such embodiments, the shell portions and resilient component can be sent to the treatment professional and the treatment professional can attach the resilient component and the shell portions together.

In such embodiments, it may be helpful for the shell portions and/or resilient component to be marked to indicate on which one or more teeth a particular shell portion is supposed to be placed and for example, in embodiments where a resilient component is pre-bent, which end of the resilient component goes on which side of the jaw of the user. Additionally, in some embodiments, one or more positions may be identified (e.g., by markings, indentations, or other manner) on the resilient component, so that the treatment profession can ascertain where each shell portion is to be positioned, for example according to a treatment plan.

Generally, the methods of the present disclosure can employ any positioners, retainers, and/or other removable appliances for finishing and/or maintaining teeth positions in connection with dental treatment that include the claimed elements. The embodiments of the present disclosure can provide a plurality of such appliances intended, for example, to be worn by a patient successively in order to achieve the gradual tooth repositioning, as described herein.

The appliance 100 can, for example, be formed from one or more shell portions each having one or more cavities shaped therein to receive one or more teeth and wherein each of the plurality of shell portions is formed to be separate from each of the other plurality of shell portions, and a resilient component attached to a side (e.g., lingual side) of at least two shell portions. The shell, or cavity provided in a portion thereof, may be designed to fit over a number of teeth (e.g., all teeth in one shell portion, all teeth in a plurality of shell portions, or less than all teeth) present in the upper or lower jaw 101 of a patient.

Figure 2:
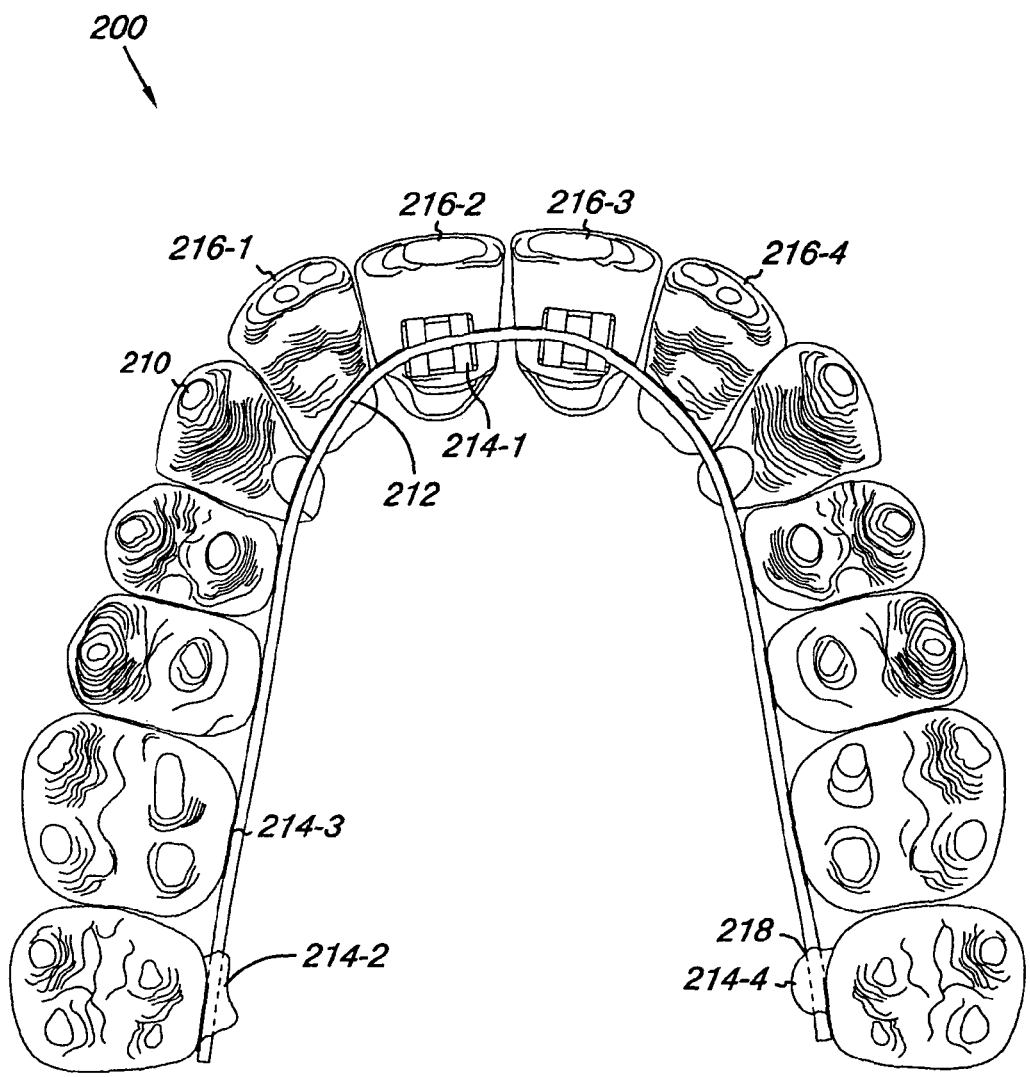
FIG. 2 illustrates an overhead view of another dental positioning adjustment appliance embodiment of the present disclosure.

FIG. 2 illustrates an overhead view of another dental positioning adjustment appliance embodiment of the present disclosure. In the embodiment of FIG. 2, the appliance 200 has a shell 210 that includes a plurality of segmented portions (e.g., 216-1, 216-2, 216-3, and 216-4, among others) and a resilient component 212.

Each portion of the shell in the embodiment illustrated in FIG. 2 includes a cavity that can receive one tooth. Such embodiments allow force to be applied to individual teeth with little or no force provided by the shell material on the other teeth in the jaw.

Force may be imparted on the other teeth via the resilient component, in some instances. In some embodiments, one or more of, the resilient component and one or more of the shell portions, can be utilized to provide one or more forces to reposition one or more teeth from a first orientation to a successive orientation.

In various embodiments, the resilient component can provide force to one or more of the first shell portion and/or the second shell portion to reposition the one or more teeth. In some embodiments, one or more of the shell portions can be designed to provide one or more forces to reposition one or more teeth received within the one or more cavities formed therein from a first orientation to a successive orientation.

A first shell portion and a second shell portion can be designed to provide one or more forces to reposition one or more teeth received within one or more cavities formed in the first or second shell portions from a first orientation to a successive orientation and the resilient component can transfer force between the first shell portion and the second shell portion to reposition the one or more teeth. In such embodiments, for example, a first cavity in the first shell portion can be used on an anchoring tooth and the shape of a second cavity or another portion of the first shell portion can be designed to impart a force. That force can then be transferred through the resilient component to the second shell portion, where the force can be applied to a tooth therein.

In some embodiments, the resilient component can provide force to at least one of the first shell portion and the second shell portion to reposition the one or more teeth. For example, in some such embodiments, the resilient component can be pre-bent such that when it is placed on the teeth of the user, the component is stretched or compressed.

In either condition, the component may be designed to attempt to return to its original shape. As the component attempts to return to its original position, force is created. This force can be used to also move teeth by connecting the resilient component to two or more shell portions as described in various embodiments of the present disclosure.

In the embodiment illustrated in FIG. 2, the resilient component is attached to the segments of the shell forming the cavities. As discussed above, the attachment can be provided in various suitable manners.

For example, the attachment may be made by affixing the resilient component to the one or more shell portions forming the plurality of cavities. Such methods of attachment can be accomplished in any suitable manner.

For instance, examples of affixed attachment mechanisms include the providing of a bracket (e.g., as illustrated at attachment member 214-1) on or secured to the shell material forming a cavity. Such brackets could be fabricated from the same material used to form the shell or a different material and could be formed at the same time as one or more of the shell portions (e.g., integrally formed with a shell portion or formed at the same time) or formed before or after the formation of the shell (e.g., affixed to a shell portion during formation of the shell portion or later via bonding, adhesive, embedding in the shell material, mechanical attachment, or other such mechanism).

In some embodiments, the attachment member can be a bracket similar to a bracket used with braces, but provided on the side of the shell portion to be located on the lingual side of a tooth. In such a manner, the bracket may not be readily viewable by people looking at the patient's mouth.

In various embodiments, the attachment member can be designed such that the resilient component can be snapped into engagement with a shell portion. For example, if the resilient component is a wire having a circular cross-section, a c-shaped clasp can be used wherein the clasp can be snapped on the wire and is sized such that friction holds the component onto the shell portion. Any suitable friction or other mechanical attachment mechanism can be utilized with various embodiment described herein.

In some embodiments, attachment may be accomplished by positioning the resilient component through an aperture formed in the shell material forming a cavity (e.g., as illustrated by aperture 218 at attachment member 214-4). In the embodiment of FIG. 2, the attachment member 214-4 is a blob of material that is formed with a hole in it.

The attachment member can be provided on the shell portion during or after formation of the shell portion. The aperture can be formed in the attachment member in any suitable manner and can be formed during or after formation of the attachment member.

In some such embodiments, the positioning can be accomplished during and/or after the formation of the shell portions. The attachment may also be made, for example, by adhering the resilient component to the plurality of cavities (e.g., as illustrated at attachment member 214-3). Examples of adhering the resilient component to the plurality of cavities include use of an adhesive material.

The attachment may also be accomplished, for example, by molding or bonding the resilient component to the plurality of cavities (e.g., as illustrated at attachment member 214-2). The molding can be accomplished by the same process used to fabricate the shell or a different process and can be accomplished during and/or after the fabrication of the shell portions.

In various embodiments, the appliance can be provided as a kit wherein it can be assembled by a treatment professional or the user. For example, one or more shell portions and a resilient component can be created (e.g., based upon patient tooth/mouth data and/or a treatment plan). The shell portions and resilient component can then be sent to the treatment profession or user, where the treatment professional or user can segment the shell portions into discrete portions having one or more cavities therein, attach and/or form one or more attachment members on the shell portions or discrete portions, and/or attach the resilient component and the shell portions or discrete portions together.

In some embodiments, the appliance includes at least one attachment member for attachment of the resilient component to at least one of the shell portions that is formed from a metallic material. In some embodiments, one or more attachment members can be formed from a polymeric material.

In various embodiments, one or more of the attachment members are transparent or colored similar to that of the tooth to which it is attached. In some embodiments, all attachment members can be the same type and, in some embodiments, one or more of the attachment members can be different types.

As described herein, in some embodiments, the shell includes a shell cavity (e.g., polymeric) formed for each tooth in an upper jaw or lower jaw. As used herein, a cavity may not fully surround a tooth or set of teeth. For example, in some embodiments, at least one of the cavities covers a top and at least portions of each of a number of side surfaces of one or more teeth. In various embodiments, a cavity may have at least portions of each of a number of side surfaces of one or more teeth.

In various embodiments, the cavities are sized to allow a patient to be able to remove the appliance without the assistance of a treatment professional and/or without the use of tools for removal of the appliance. Such an embodiment can be beneficial in allowing the patient to remove the appliance for cleaning of the appliance or their teeth or for temporary removal, such as for a date or big event or meeting or for wearing the appliance when at home and removing the appliance at work, among other benefits.

Figure 3:
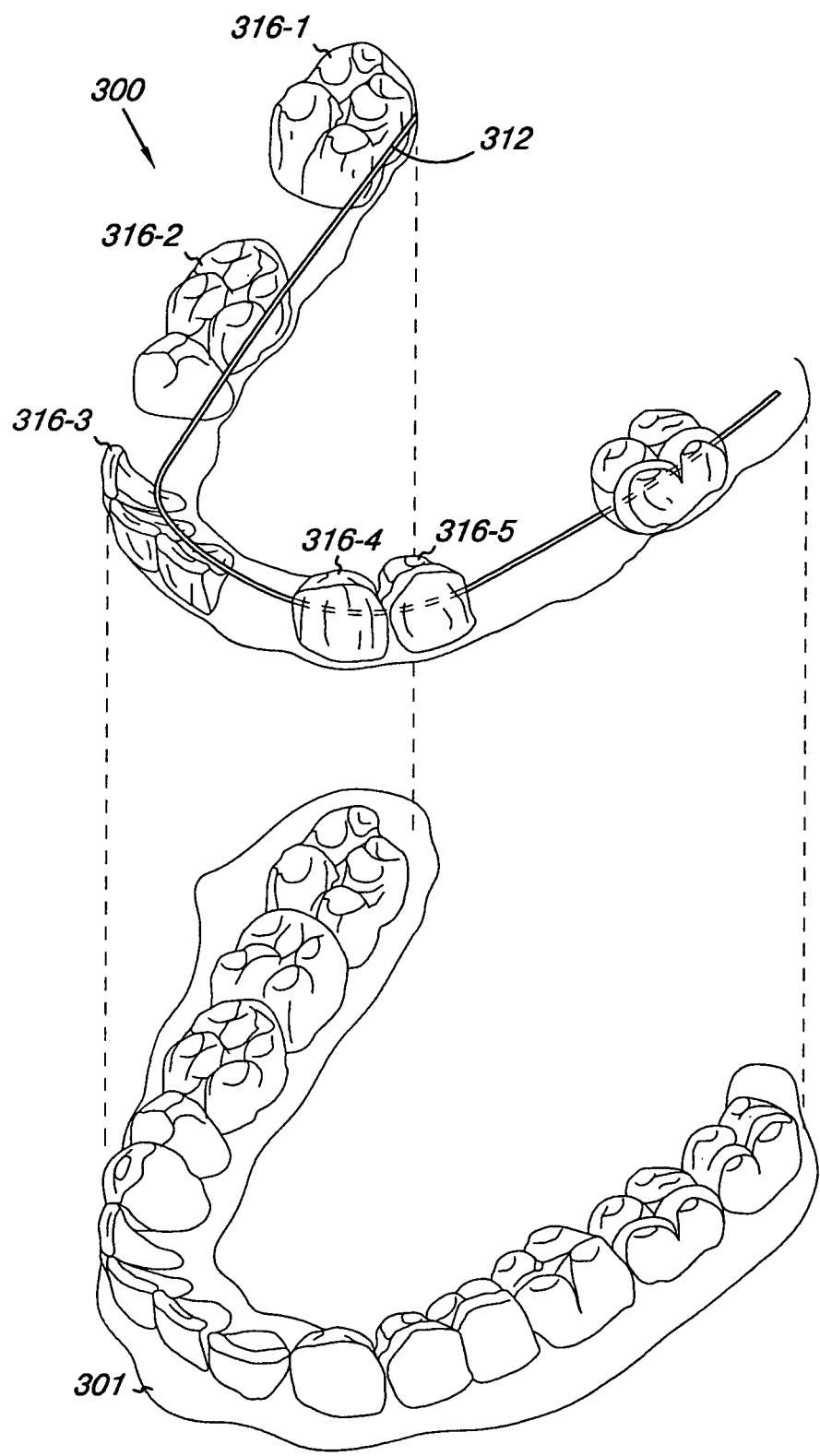
FIG. 3 illustrates a lower jaw of a patient together with another example of a dental positioning adjustment appliance embodiment of the present disclosure.

FIG. 3 illustrates a lower jaw of a patient together with another example of a dental positioning adjustment appliance embodiment of the present disclosure. In the embodiment of FIG. 3, the appliance 300 includes a shell formed from a plurality of shell segments 316 defining a number or cavities for the receiving of one or more teeth of the jaw 301 therein and a resilient component 312.

The shell segments are attached to the teeth via one or more attachment members. As described above, an attachment member can be provided in any suitable manner and can span a portion of the surface of a shell segment for receiving one tooth or can span a surface for receiving more than one tooth.

In some embodiments the resilient component can have a preformed bent shaped portion that was shaped based upon a treatment plan. As discussed herein, a treatment plan can be determined at the beginning of treatment of a patient (e.g., for the alignment of teeth) and can be accomplished through use of one or more appliances.

Where multiple appliances are to be used, the preformed shapes of the resilient component can be designed to allow the appliances to be used serially (e.g., to move one or more teeth to a first configuration with a first appliance and to move one or more teeth to a second configuration with a second appliance, and so on until a final configuration is reached).

In some embodiments, the resilient component can be a super-elastic component. For example, a resilient component formed from a shape memory alloy such as copper-zinc-aluminum-nickel, copper-aluminum-nickel, and nickel-titanium, among other super-elastic materials. Such embodiments can enable an appliance to provide more movement and/or more force than an appliance that uses a polymeric elastomer, in some situations.

In some situations, certain individual and/or sets of teeth can be repositioned while other teeth can provide a base and/or anchor region for holding the repositioning appliance in place as it applies the resilient repositioning force against the tooth or teeth to be repositioned. In some cases, many or most of the teeth can be repositioned at some point during the treatment.

In such cases, one or more of the teeth to be moved also can serve as a base and/or anchor region for holding the repositioning appliance. Additionally, the gums (e.g., the gingiva), the palate, and/or other surrounding tissue or bones can contribute to serving as an anchor region, thus allowing all or nearly all of the teeth to be repositioned at the same time.

In embodiments such as is illustrated in FIG. 3, in some instances, a number of teeth can be used as an anchor. Those skilled in the art will understand that there are many anchoring arrangements that can be created with the embodiments of the present disclosure.

For instance, a cavity receiving multiple teeth (e.g., 316-2 for receiving two teeth, 316-3 for receiving three teeth) can be used as an anchor for moving a single tooth within another cavity (e.g., 316-1 for receiving a single tooth). In another example, a tooth that is more secure can be used to move a less secure tooth by positioning distinct cavities (e.g., 316-4 around the more secure tooth and 316-5 around the less secure tooth) around each of the teeth and using the more secure one as an anchor for moving the less secure one, among other anchoring arrangements.

Figure 4:
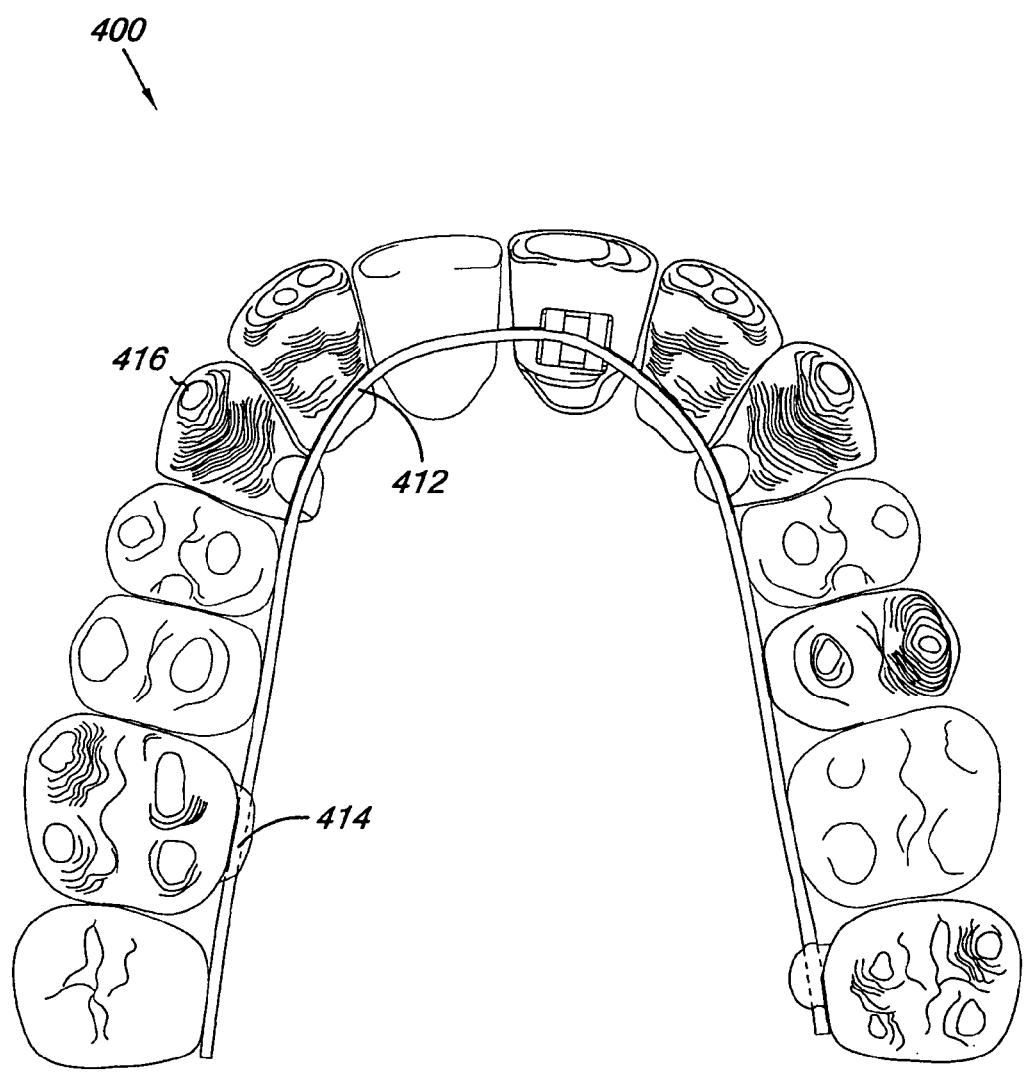
FIG. 4 illustrates an overhead view of a lower jaw of a patient together with an example of a dental positioning adjustment appliance embodiment similar to FIG. 3 positioned thereon.

FIG. 4 illustrates an overhead view of a lower jaw of a patient together with an example of a dental positioning adjustment appliance embodiment similar to FIG. 3 positioned thereon. In the embodiment of FIG. 4, the appliance 400 includes a plurality of shell portions 416 that each includes a cavity for receiving one or more teeth. Each portion 416 of the shell is attached to a resilient component 412 via an attachment member 414.

In such an embodiment, the cavities can be designed to be fit over specific teeth and therefore the fit of the appliance can be customized to a particular patient. Such embodiments can also be specialized to target particular movements of specific teeth without applying force to other specific teeth.

This can be advantageous in some instances, such as when a tooth has been moved and is in the process of settling in its new position. During such a period, the tooth can be more easily moved than if it had not been recently moved.

Accordingly, in some instances, force applied to that tooth may move the tooth in an unintended manner. However, with such embodiments, a particular tooth may not have a cavity provided to receive it and therefore force on that particular tooth may be reduced or eliminated, in some instances.

In various embodiments, the embodiment can be a removable dental positioning appliance kit. The kit can, for example, include a first set of appliance components having a first plurality of shell portions each having one or more cavities shaped therein to receive one or more teeth and a first resilient preformed bent shaped component for attachment to a side of at least two shell portions that was shaped based upon a treatment plan shaped in order to position the one or more teeth during a first stage of treatment. In some embodiments, the appliance kit can include a second set of appliance components having a second plurality of shell portions each having one or more cavities shaped therein to receive one or more teeth and a second resilient preformed bent shaped component for attachment to a side of at least two shell portions that was shaped based upon a treatment plan shaped in order to position the one or more teeth during a second stage of treatment.

In some embodiments, the second plurality of shell portions includes at least one shell portion from the first plurality of shell portions. In such embodiments, it may be the case that the cavities can be reused from one stage to another and therefore, the second plurality of shell portions may include one or more of the first plurality of shell portions.

In various embodiments, the resilient component may be reused. For example, the second resilient preformed bent shaped component referenced above could be the first resilient preformed bent shaped component. In some such instances, the shell portions may be changed, for example, to alter the forces provided by the shell portions themselves or in combination with another shell portion or the resilient component. In some such embodiments, the resilient component may be reshaped by a treatment professional.

In some embodiments, the kit can include multiple resilient preformed bent shaped components wherein each resilient preformed bent shaped component is preformed before being provided to the treatment professional in order to position the one or more teeth during a particular stage of treatment based upon a treatment plan. In such embodiments, it may allow the treatment professional to remove the appliance from the user's mouth, remove the shell portions, from a first resilient component, attach the shell portions to another resilient component, and reposition in the user's mouth.

Such embodiments may reduce the amount of tools, time, skill by the treatment professional, and/or guesswork regarding bending of the resilient component (e.g., because the pre-bending is based upon a predetermined treatment plan and/or the bending is aided by computerized calculation of bend location and angle).

Additionally, in some embodiments, the kit may come with a resilient component that is not pre-bent or where it is simply bent into a generally arcuate shape without other bends. In such embodiments, the positioning of the attachment members on the surface of the teeth to be positioned can be used to aid in the application of force in one or more directions on the tooth to which the member is attached or to other teeth.

In some embodiments, the design of the attachment members can be manufactured to position the member on a tooth in such a position. For example, the shape of the attachment member can be designed differently so that its attachment with the tooth and/or resilient component provide one or more different forces as compared to forces provided by an attachment member that is not specially designed. Changes in the design can include, for example, a change in an exterior surface shape, a change in the orientation in one or more axes (e.g., X, Y, and/or Z axes in a Cartesian coordinate system) of the portion of the member that receives the resilient component.

In some embodiments, the position of the attachment member on the tooth can be changed. For example, the attachment member can be move toward the posterior of the tooth.

This can be accomplished by indicating such a change to the treatment professional that is to attach the attachment member or can be accomplished by designing the shape of the attachment member such that when positioned, the attachment member compliments the position on the tooth at which it is to be positioned. This can be accomplished by having a surface that contacts the tooth that is specifically designed to compliment a particular contour of a portion of the tooth or by having an attachment mechanism (such as a ring that seats around the circumference of the tooth) that is shaped such that there is only on orientation in which the ring seats correctly, among other possible mechanisms that could be used for positioning the attachment member.

In some embodiments, the design can be based upon a treatment plan that is to be implemented. In such embodiments, the attachment members can provide the particular force to be used in the treatment plan and this allows for more precise positioning of the teeth, in some instances. Embodiments without a pre-bent resilient component can be beneficial because the component does not have to be bent by a treatment professional or pre-bent and therefore, it may be less time consuming and easier to install, in some instances.

Figure 5:
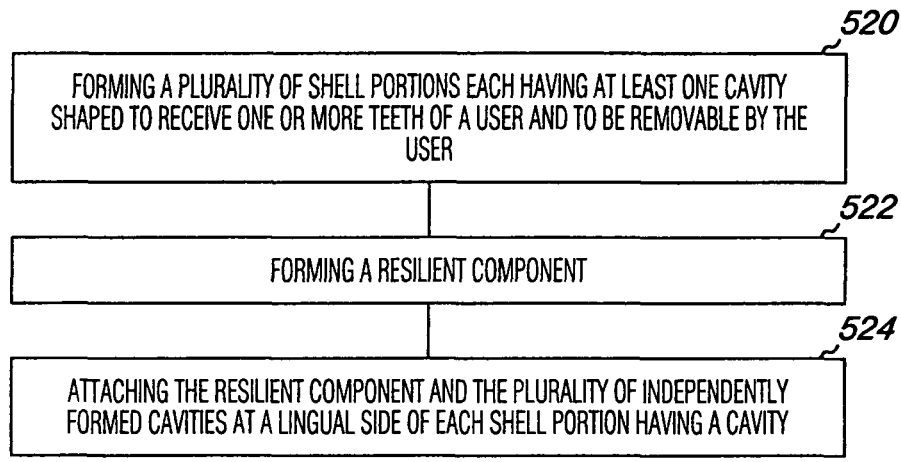
FIG. 5 illustrates a method embodiment of forming a removable dental positioning appliance according to the present disclosure.

FIG. 5 illustrates a method embodiment of forming a removable dental positioning appliance according to the present disclosure. The method embodiment includes, forming a plurality of shell portions each having at least one cavity shaped to receive one or more teeth of a user and to be removable by the user, at block 520.

The method embodiment of FIG. 5 also includes, forming a resilient component, at block 522. In some embodiments, the method can include preforming the resilient component. For example, the resilient component can be preformed to provide a range of resilient movement according to at least a portion of a treatment plan.

At block 524, the method embodiment includes, attaching the resilient component and the plurality of independently formed cavities at a lingual side of each shell portion having a cavity. In some embodiments, the shell portion can be created and a resilient component can be attached thereto, for example, before or after separation of the shell portion into smaller segments, as discussed above.

As used herein independently means that the cavities are separate from each other and can move with respect to each other. This concept is also described herein where the cavities are discretely formed or separated.

Such formation can be accomplished by creating the shell portions as separate portions or by creating one or more shell portions and segmenting the shell portions into smaller portions. For example, a shell portion can be fabricated having cavities for four teeth and such a portion can be segmented into smaller portions each having less than four cavities (e.g., segmented into four smaller portions each having one cavity formed therein, segmented into portions having two cavities each, or segmented into two portions with one having three cavities and one having one cavity).

In some embodiments, the method includes attaching a number of attachment members to the shell in order to accomplish the attaching of the resilient component and the polymeric shell at a lingual side of the shell. In such embodiments, the attachment members can be brackets, adhesives, or other mechanisms (e.g., bonding, welding, etc.) that can be applied to the shell in order to accomplish attachment.

In various embodiments, the attachment of the resilient component to the portions forming cavities includes feeding the portions forming cavities onto the resilient component through attachment members formed on each of the portions. For example, in embodiments where the attachment members include apertures, or some other types of frictionally or adhesively attached configurations, the resilient component can be attached by feeding the portions through the attachment members.

In some embodiments, forming the polymeric shell includes forming a number of attachment members thereon for attaching the resilient component and the polymeric shell at a lingual side of the shell. In such embodiments, the attachment members can include brackets, apertures, and other such suitable attachment mechanisms that can be formed on the shell.

Figure 6:
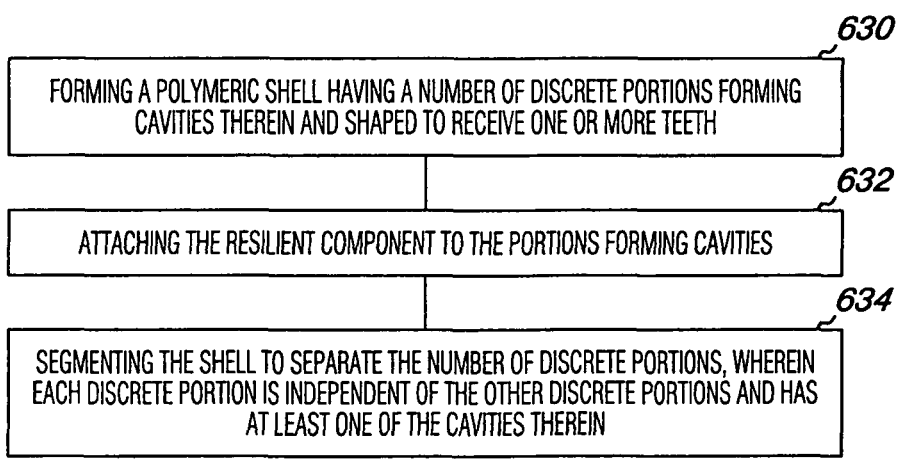
FIG. 6 illustrates another method embodiment of forming a removable dental positioning appliance according to the present disclosure.

FIG. 6 illustrates another method embodiment of forming a removable dental positioning appliance according to the present disclosure. The method embodiment includes, forming a polymeric shell having a number of discrete portions forming cavities therein and shaped to receive one or more teeth, at block 630.

The method embodiment of FIG. 6 also includes attaching the resilient component to the portions forming cavities, at block 632. At block 634, the method embodiment includes, segmenting the shell to separate the number of discrete portions, wherein each discrete portion is independent of the other discrete portions and has at least one of the cavities therein.

In some embodiments, the method can include segmenting the shell to form the number of discrete portions by various manners. Any suitable manner can be used to segment the shell. Laser cutting is one such suitable example. In such embodiments, each discrete portion can include one or more cavities shaped to receive one or more teeth from a first orientation to a successive orientation based upon a predetermined treatment plan.

As discussed above, in some embodiments, the shell can be formed in whole or in part from a number of suitable materials. For example, one or more of the discrete portions of the shell or portions thereof can be formed from a substantially transparent and/or polymeric material. In some embodiments, the buccal side of the discrete portions of the shell can be formed from a substantially transparent polymeric material. In some embodiments, segmenting the shell to form the number of discrete portions can be accomplished before attaching the resilient component to the portions forming cavities.

As will further be appreciated by one of ordinary skill in the relevant art, various features are grouped together in the description of the present disclosure in a single embodiment for the purpose of streamlining the disclosure. This method of disclosure, however, is not to be interpreted as reflecting an intention that the embodiments of the disclosure require more features than are expressly recited in each of the following claims. Rather, as the claim recitations reflect, inventive subject matter lies in less than all features of a single disclosed embodiment.

Hence, predetermining a treatment plan with a virtual model as described in the present disclosure may be a recommended and claimed methodology, however, just forming and/or using an aligner as described in the disclosure and as recited in the following claims is intended as novel subject matter to be protected. For example, novel subject matter as described in the present disclosure can be included in a portion of an aligner, rather than the whole aligner, and remain consistent with the teachings of the present disclosure.

Unless explicitly stated, the method embodiments described herein are not constrained to a particular order or sequence. Additionally, some of the described method embodiments, or elements thereof, can occur or be performed at the same, or at least substantially the same, point in time.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A removable dental positioning appliance, comprising:
a plurality of at least three shell portions positionable in a patient's mouth at a same time and usable during a first orientation, each having a number of individual cavities shaped therein to receive and completely cover an occlusal surface and labial and lingual surfaces toward a gingival line of one tooth per individual cavity and wherein each of the plurality of at least three shell portions is formed to be separate from each of the other plurality of shell portions and reusable from the first orientation to a successive orientation; and
a pre-bent resilient component releasably attached to the plurality of shell portions via a number of attachment members located on the plurality of shell portions;
wherein at least one of the pre-bent resilient component, and one or more of the plurality of shell portions at the same time provides one or more forces to reposition one or more teeth from the first orientation to the successive orientation.

2. The appliance of claim 1, wherein the pre-bent resilient component is attached to a lingual side of the plurality of at least three shell portions.

3. The appliance of claim 1, wherein the number of attachment members are formed from a material selected from a group including a metallic material and a polymeric material.

4. The appliance of claim 1, wherein at least one of the plurality of shell portions is designed to provide one or more forces to reposition one or more teeth received within the individual cavity formed therein from the first orientation to the successive orientation.

5. The appliance of claim 1, wherein a first shell portion and a second shell portion of the plurality of at least three shell portions are designed to provide one or more forces to reposition the tooth received within the individual cavity formed in the first or second shell portions from a first orientation to a successive orientation and wherein the pre-bent resilient component transfers force between the first shell portion and the second shell portion to reposition the one or more teeth.

6. The appliance of claim 5, wherein the pre-bent resilient component provides force to at least one of the first shell portion, the second shell portion and the third shell portion to reposition the one or more teeth.

7. The appliance of claim 1, wherein the pre-bent resilient component is a wire having a preformed bent shaped portion that was shaped based upon a treatment plan.

8. The appliance of claim 1, wherein the number of individual cavities cover a top and portions of each of a number of side surfaces of a tooth.

9. The appliance of claim 1, wherein the pre-bent resilient component is a super-elastic component.

10. A method of forming a removable dental positioning appliance, the method comprising:
   forming a plurality of at least three shell portions positionable in a patient's mouth at a same time and usable during a first orientation, each having a number of individual cavities shaped therein to receive and completely cover an occlusal surface and labial and lingual surfaces toward a gingival line of one tooth per individual cavity, wherein each of the plurality of at least three shell portions is formed to be separate from each of the other plurality of shell portions and reusable from the first orientation to a successive orientation;
   forming a pre-bent resilient component releasably attached to the plurality of at least three shell portions at the same time via a number of attachment members located on the plurality of at least three shell portions; and
   attaching the pre-bent resilient component and the plurality of at least three shell portions, wherein at least one of the pre-bent resilient component, and one or more of the plurality of shell portions provides one or more forces to reposition one or more teeth from the first orientation to the successive orientation.

11. The method of claim 10, wherein the method includes preforming the pre-bent resilient component to provide a range of resilient movement according to at least a portion of a treatment plan.

12. The method of claim 10, wherein the method includes attaching a number of attachment members to the plurality of at least three shell portions in order to accomplish the attaching of the pre-bent resilient component and the plurality of at least three shell portions at a lingual side of each shell portion.

13. The method of claim 10, wherein forming the plurality of at least three shell portions includes forming a number of attachment members thereon for attaching the pre-bent resilient component and the plurality of at least three shell portions.

14. A method of forming a removable dental positioning appliance, the method comprising:
   forming a polymeric shell having a plurality of at least three discrete shell portions positionable in a patient's mouth at a same time and usable during a first orientation, forming, in each, a number of individual cavities shaped therein to receive and completely cover an occlusal surface and labial and lingual surfaces toward a gingival line of one tooth per individual cavity, wherein each of the plurality of at least three shell portions is formed to be separate from each of the other plurality of shell portions and reusable from the first orientation to a successive orientation;
   releasably attaching a pre-bent resilient component to the plurality of at least three discrete shell portions at the same time via a number of attachment members located on the plurality of at least three shell portions, where at least one of the pre-bent resilient component, and one or more of the plurality of shell portions provides one or more forces to reposition one or more teeth from the first orientation to the successive orientation; and
   segmenting the polymeric shell to separate the plurality of at least three discrete shell portions, wherein each of the plurality of at least three discrete shell portions in independent of the others and has at least one of the cavities therein.

15. The method of claim 14, wherein segmenting the polymeric shell to separate the plurality of at least three discrete shell portions is accomplished before releasably attaching the pre-bent resilient component to the plurality of at least three discrete shell portions.

16. The method of claim 14, wherein segmenting the polymeric shell to separate the plurality of at least three discrete shell portions is accomplished by laser cutting.

17. The method of claim 14, wherein forming the polymeric shell includes forming the polymeric shell from a substantially transparent polymeric material.

18. The method of claim 14, wherein forming the polymeric shell includes forming a buccal side of the polymeric shell from a substantially transparent polymeric material.

19. The method of claim 14, wherein the successive orientation is based upon a predetermined treatment plan.

20. A removable dental positioning appliance kit, comprising:
   a first set of appliance components, including:
      a first set of at least three shell portions positionable in a patient's mouth at a same time and usable during a first stage of treatment, each having one or more cavities shaped therein to receive and completely cover an occlusal surface and labial and lingual surfaces toward a gingival line one tooth per cavity, wherein each of the first set of shell portions is formed to be separate from each of the other shell portions within the first set; and
      a first resilient preformed bent shaped component releasably attached to a lingual side of each of the first plurality of shell portions at the same time via a number of attachment members located on the first set of shell portions, wherein the first resilient preformed bent shaped component is preformed based upon a treatment plan in order to position one or more teeth during a first stage of treatment,
      the first resilient preformed bent shaped component adapted to be replaced while one or more of the shell portions within the first set remain in place or one or more of the shell portions within the first set adapted to be replaced while the first resilient preformed bent shaped component remains in place.

21. The appliance kit of claim 20, wherein the kit includes:
   a second set of appliance components, including:
      a second set of shell portions each having one or more cavities shaped therein to receive one or more teeth, wherein each of the second set of shell portions is formed to be separate from each of the other second set of shell portions; and
      a second resilient preformed bent shaped component releasably attached to a side of at least two shell portions that was shaped based upon a treatment plan in order to position the one or more teeth during a second stage of treatment.

22. The appliance kit of claim 21, wherein the second set of shell portions includes at least one shell portion from the first set of shell portions.

23. The appliance kit of claim 21, wherein a number of the first plurality of shell portions are removed from the first resilient preformed bent shaped component after the first orientation and reused for the successive orientation by attaching the number of the plurality of shell portions to a second resilient preformed bent shaped component.

24. The appliance kit of claim 20, wherein the kit includes multiple resilient preformed bent shaped components wherein each resilient preformed bent shaped component is preformed before being provided to the treatment professional in order to position one or more teeth during a particular stage of treatment based upon the treatment plan.

* * * * *